US00PP22504P3

(12) United States Plant Patent
Maillard et al.

(10) Patent No.: US PP22,504 P3
(45) Date of Patent: Feb. 21, 2012

(54) NECTARINE TREE NAMED 'NECTARFLORA'

(50) Latin Name: ***Prunus persica* var. *nucipersica***
Varietal Denomination: NECTARFLORA

(75) Inventors: Arsene Maillard, Elne (FR); Laurence Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 0 days.

(21) Appl. No.: 12/662,970

(22) Filed: May 13, 2010

(65) Prior Publication Data

US 2010/0299792 P1 Nov. 25, 2010

(30) Foreign Application Priority Data

May 18, 2009 (QZ) ..... 2009/0933

(51) Int. Cl.
*A01H 5/00* (2006.01)

(52) U.S. Cl. ..... Plt./188

(58) Field of Classification Search ..... Plt./188
See application file for complete search history.

*Primary Examiner* — June Hwu

(74) *Attorney, Agent, or Firm* — Westerman, Hattori, Daniels & Adrian, LLP

(57) ABSTRACT

A new and distinct variety of nectarine tree, denominated 'NECTARFLORA', has fruits of very long shelf life without alteration before and after harvesting, a semi-sweet white flesh of high eating quality and an attractive red skin. Fruits can be consumed crunchy or melting.

4 Drawing Sheets

Botanical classification: *Prunus persica* var. *nucipersica*.
Variety denomination: 'NECTARFLORA'.

This application claims priority of Community plant variety right No. 2009/0933 filed on May 18, 2009, which is hereby incorporated by reference in its entirety.

BACKGROUND OF THE NEW VARIETY

The present invention relates to a new and distinct variety of nectarine tree, *Prunus persica* var. *nucipersica*, which has been given the variety denomination 'NECTARFLORA'. This new tree produces fruit with a long shelf life without alteration both on the tree after growth completion and after harvesting, very good eating quality, clingstone white flesh fruit for fresh market in June in the Pyrénées-Orientales departement, France. Contrast is made to 'Nectarjune' (U.S. Plant Pat. No. 19,379), a white nectarine variety, and to its parents, 'Maillarduchesse' (non-patented) white nectarine tree and 'Nectaprima' (U.S. Plant Pat. No. 17,583) yellow nectarine tree, for reliable description. 'NECTARFLORA' is a promising candidate for commercial success in that it has very attractive fruits with very long shelf life without alteration before after harvesting.

ORIGIN OF THE VARIETY

The 'NECTARFLORA' white nectarine tree originated in a cultivated area of the south of France, in the Pyrénées-Orientales departement, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontagne': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'NECTARFLORA' variety resulted from a pollinated cross between the 'Maillarduchesse' (non-patented) white nectarine tree, which was used as the seed parent, and the Nectaprima' (U.S. Plant Pat. No. 17,583) yellow nectarine tree, which was used as the pollen parent. 'NECTARFLORA' was provisionally designated, tested and genetically identified by a genetic profile, under number 05.02.109 NB ASF 0624 and was registered at the Official Catalogue of the Agriculture Ministry of the French Republic on Dec. 1, 2008 under number 1028957. It was obtained by hybridizing and propagated by grafting on a 'Franc Inra Montclar' (non-patented) or 'Cadaman' (non-patented) or 'INRA GF 677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety of nectarine tree blooms at the end of February at Perpignan in the Pyrénées-Orientales departement, France. More particularly, it blooms between February 20$^{th}$ and March 5$^{th}$, generally about 7 to 10 days before 'Nectarjune' (U.S. Plant Pat. No. 19,379).

The first fruit of 'NECTARFLORA' nectarine tree ripens in June, generally about 5 to 10 days before 'Nectarjune' (U.S. Plant Pat. No. 19,379). More particularly, it approximately ripens between June 15$^{th}$ and 25$^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
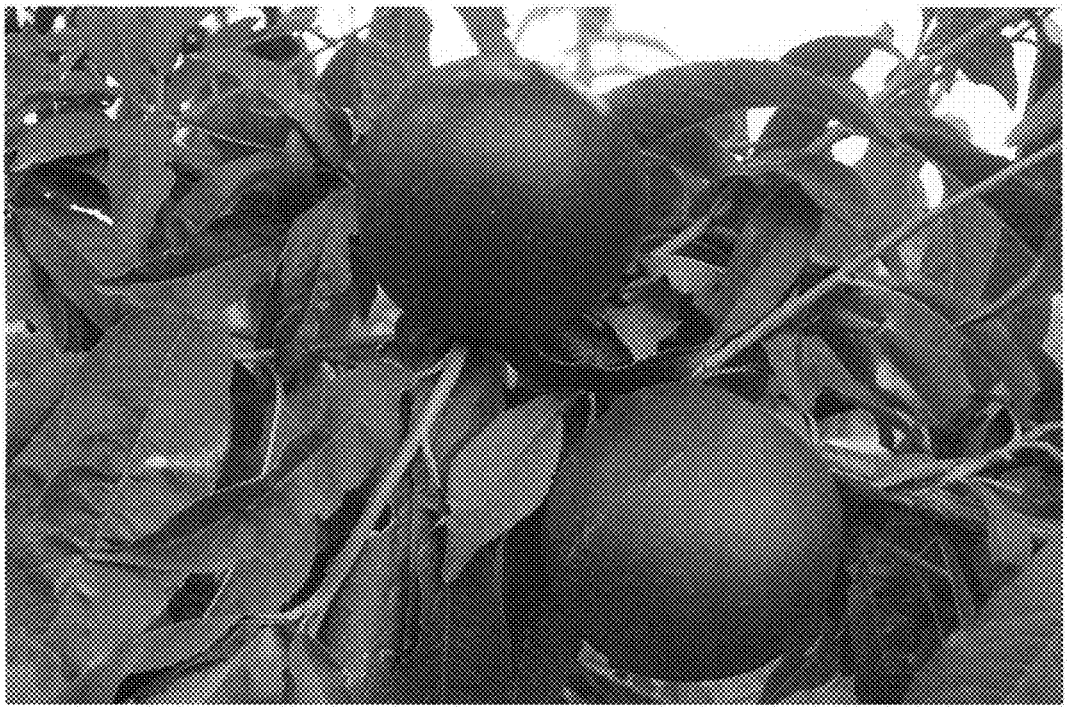
FIG. 1 is a color photograph, which shows typical fruit specimens on a tree of the new variety and leaves of the new variety in orchard.
Figure 2:
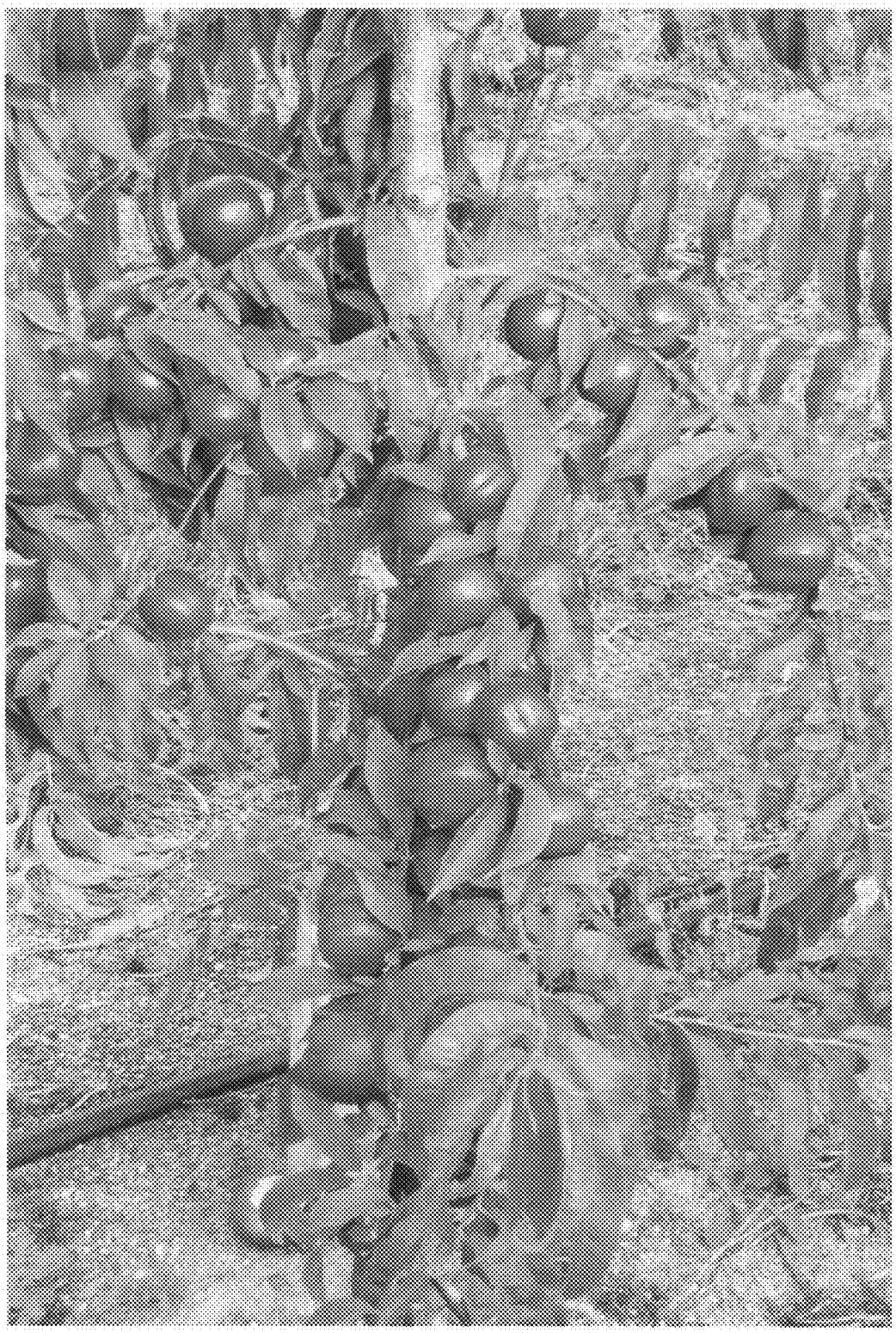
FIG. 2 is a color photograph, which shows a view of a tree of the new variety in orchard, bearing fruits.
Figure 3:
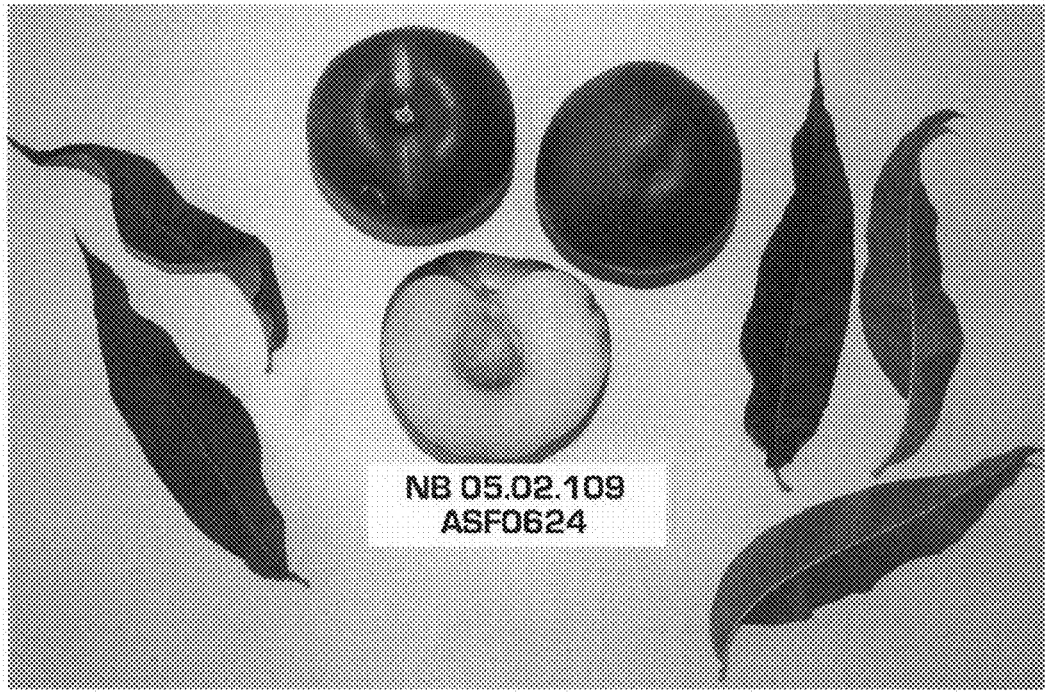
FIG. 3 is a color photograph, which shows two whole fruits and leaves of the new variety, and a third fruit, cut in half with the pit left in the half for depicting the fruit flesh, the pit and the stone of the new variety.
Figure 4:
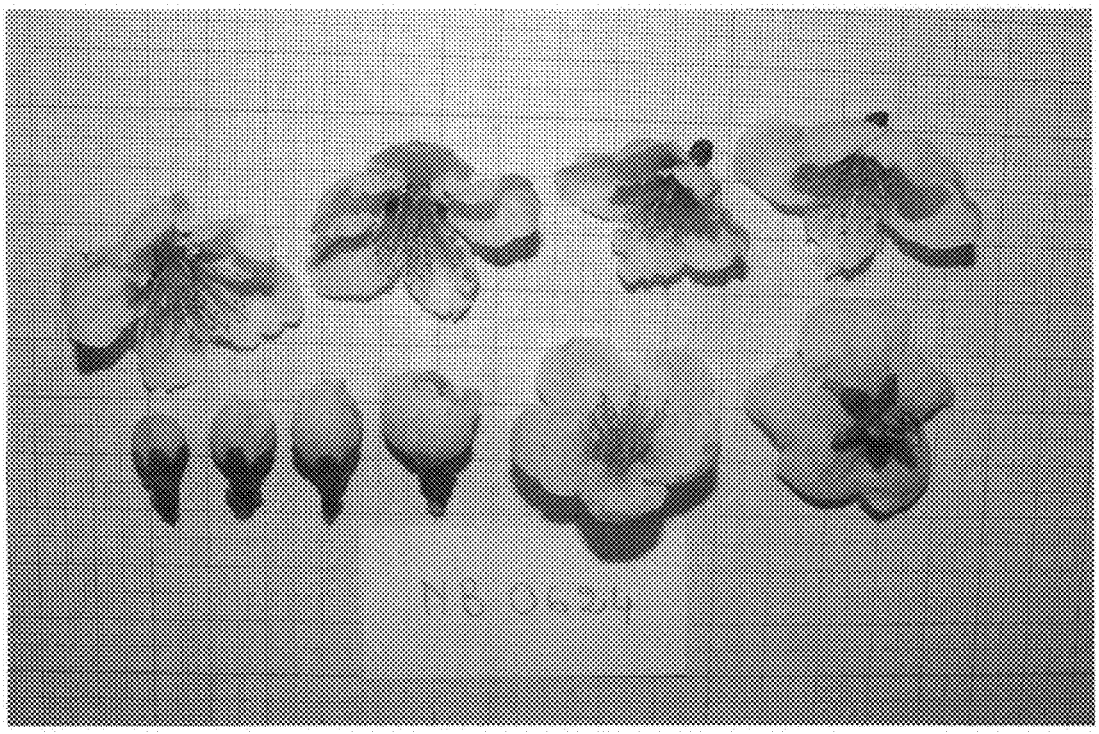
FIG. 4 is a color photograph with reverse and side views of flowers of the new variety, and, with petals removed, reproductive organs of the new variety.

Due to chemical development, processing and printing, the leaves and fruit depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruit by 'NECTARFLORA' is high, due to fruit very long shelf life without alteration after harvesting.

Trees are vigorous and large stature half-standing in a semi-spread to semi-upright out aspect. The anthocyanic coloration of flowering shoot is present excluding brushwood side away from sun. Flowering begins early in springtime. The type of flower is showy with medium petal size. Petals are light pink. Leaf glands are present and round. Time of maturity for consumption is early. The fruit flesh is white and its skin is very thick, with a purple red blush and a pink-washed red background. The stone is medium size. Fruit taste is semi-sweet, very aromatic and with a high level of sugars.

Compared to 'Nectarjune' (U.S. Plant Pat. No. 19,379) white nectarine tree, 'NECTARFLORA' variety has an earlier time of blooming and time of maturity, as set forth above. Both varieties have the same amount of flowers. However, 'NECTARFLORA' fruits are superior to 'Nectarjune' fruits both in their presentation and size.

The new variety male parent, which is 'Nectaprima' (U.S. Plant Pat. No. 17,583), produces yellow nectarines instead of white nectarines. 'Nectaprima' comparatively ripens about 17 days earlier than the new variety. It was chosen as a genitor because of the interesting color of its semi-sweet fruits and their very high gustative quality. 'Nectaprima' fruits have an aromatic and sweet taste for semi-sweet fruits.

The new variety female parent, which is the 'Maillarduchesse' (non-patented) white nectarine tree, produces white nectarines of balanced taste, instead of semi-sweet taste for the new variety. 'Maillarduchesse' ripening comparatively begins later than the new variety's ripening, generally around September 8$^{th}$.

DETAILED DESCRIPTION

Referring more specifically to the pomological details of this new and distinct variety of nectarine tree, the following was observed on trees in their third growing season (second year of production) under the ecological conditions prevailing at the orchards located near the town of Elne, Pyrénées-Orientales departement, France. All observations have been done on rootstock cultivars. Used rootstocks were 'Franc Inra Montclar' (non-patented) trees or 'Cadaman' (non-patented) trees or 'INRA GF 677' (non-patented) trees. All major color code designations are by reference to The R.H.S. Color Chart (Fourth Edition) provided by The Royal Horticultural Society of Great Britain.

Tree:

*Size.*—Generally. — Considered large. The tree size the first year was approximately 240 cm. The tree was pruned during each following dormant season to a height of approximately 250 cm. Current season shoots growth could reach 60 to 80 cm. The tree size from the second year (second and next years) reached a final height of 310 to 330 cm with current season shoots length comprised.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor.*—Considered vigorous.

*Productivity.*—Very Productive. Fruit set is spaced by thinning to develop the remaining fruit into the desired market sized fruit. The number of the fruit set varies with the prevailing climatic conditions and cultural practices employed during the bloom period, and is therefore not distinctive of the present variety.

*Bearer.*—Very regular. Thinning of 2 fruits out of 3 was necessary for the tree valorisation. Thinning was necessary every year during the years of observation.

*Form.*—The 'NECTARFLORA' variety has naturally a semi-spread to semi-upright shape.

*Density.*—Considered dense.

*Hardiness.*—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter.*—Approximately between 6.0 cm and 7.0 cm in diameter when measured at a distance of approximately 30 cm above the soil level.

*Bark texture.*—Considered slightly rough, with folds of papery scarfskin being present.

*Lenticels.*—Numerous lenticels are present. The lenticels range in size from approximately 4.0 millimeters to 6.0 millimeters in width, and from 1.5 millimeters to 2.0 millimeters in height.

*Lenticel color.*—The outside of lenticels has a silver-grey color (RHS Grey 201 C), whereas the inside is considered brown (RHS Greyed Orange 166B).

*Bark coloration.*—The bark has a silver-grey color a little more pronounced than lenticels outside color (RHS Grey 201 C or RHS Black 202 C).

Branches:

*Size.*—Mature branches and current season shoots are considered medium for the variety.

*Diameter.*—Average as compared to other nectarine varieties. The current season shoots have a diameter from 5.0 to 7.0 millimeters, and mature branches have a diameter comprised between 12.0 and 23.0 millimeters.

*Surface texture.*—Average, wood which is several years old has no furrowed appearance.

*Crotch angles.*—Primary branches are considered variable, but the crotch angles are generally between 60 degrees and 90 degrees from the horizontal axis. This particular characteristic is not considered distinctive of the variety, however.

*Current season shoots.*—Surface texture. — Substantially glabrous.

*Internode length.*—Generally 30.0 millimeters to 40.0 millimeters.

*Color of mature branches.*—Medium brown (RHS Grey Brown 199 A to B).

*Current seasons shoots.*—Color. — The color of new shoot tips is considered a light green (RHS Green 143 C to D or RHS 145 D) on lower part of new shoot tips, whereas the upper part is colored in more or less brown-red (varying from RHS Greyed Red 182 A to C).

Leaves:

*Size.*—Considered medium to large for the species. The ratio leaf length/leaf width is above 4.

*Leaf length.*—Approximately 165.0 to 175.0 millimeters with leaf petiole.

*Leaf width.*—Approximately 38.0 to 42.0 millimeters.

*Leaf base shape.*—Concave.

*Leaf form.*—Lanceolate.

*Leaf tip form.*—Acuminate.

*Leaf color.*—Upper leaf surface. — Dark Green (RHS Green 137 A). Lower surface. — Medium Green (RHS Green 137 B to 137 C).

*Leaf texture.*—Smooth and glabrous.

*Leaf venation.*—Pinnately veined.

*Mid-vein.*—Color. — Light green with a cream touch (RHS Yellow Green 145 D).

*Leaf margins.*—Slightly undulating.

*Form.*—Considered slightly dentate.

*Uniformity.*—Leaves are isolated or grouped by 2 or 3. In this last case, one leaf of normal size is found with one or two smaller leaves (at least 50% smaller).

*Leaf petioles.*—Size. — Considered medium. Length. — About 8.0 to about 10.0 mm. Diameter. — About 2.0 mm. Color. — Light green shading to white (RHS Yellow Green 145 B to C).

*Leaf glands.*—Size. — Considered small to medium. Their length is about 1.0 millimeters. Number. — Generally 2 to 4 glands per leaf. Type. — Round. Color. — On young leaves, leaf glands color is considered a pale green (RHS Green 145 B). On older leaves, leaf glands color turn to a dark brown (RHS Grey Brown 199 A to 199 B).

*Leaf stipules.*—Generally. — No leaf stipules were observed. But as seen in the characteristic relative to the leaves uniformity, it is possible to find leaves by groups of 2 or 3, with a normal-size leaf and smaller ones.

Flowers:

*Flower buds.*—Generally. — At pre-floral stage of development, the floral buds are conic in form with a round tip. Their form is evolving until blooming, with variables dimensions. Just before blooming, floral buds are approximately 11.0 millimeters wide and approximately 18.0 millimeters long.

*Flower buds.*—Color. — This characteristic is dependent upon the proximity to bloom. At pre-floral stage of development, the bottom of the flowers buds, formed by the sepals, is of purple-brown color (RHS Greyed Purple 183 A to B or Grey Brown Group 199 A); the corolla, formed by the petals, is generally of pale pink color (RHS Red Purple 69 A to C). Petals color shows an evolution until the end of flowering. The buds are considered hardy under typical central Pyrénées-Orientales departement climatic conditions.

*Hardiness.*—No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—Generally end of February to beginning of March. The first bloom was observed on Feb. 21, 2003.

*Blooming time.*—Considered early-season in relative comparison to other commercial nectarine cultivars grown in the Pyrénées-Orientales departement, France. The date of full bloom is observed on March. The date of bloom varies slightly with climatic conditions and cultural practices. Thus the first full bloom was observed approximately on Feb. 27, 2003. Last observed blooming times were from Feb. 24, 2007 to Mar. 3, 2007, then from Feb. 18, 2008 to Feb. 27, 2008, then from Feb. 21, 2009 to Mar. 6, 2009.

*Duration of bloom.*—Approximately 12 days. This characteristic varies slightly with the prevailing climatic conditions.

*Flower type.*—The variety is considered to have a showy type flower.

*Flower size.*—Considered medium. Flower diameter at full bloom is approximately 32.0 to 42.0 millimeters.

*Bloom quantity.*—Considered abundant, approximately 40 to 45 flowers per meter.

*Flower bud frequency.*—Generally 2 flower buds appear per node, occasionally 1.

*Petal size.*—Generally. — Considered medium for the species.

*Length.*—Generally about 22.0 millimeters.

*Width.*—Generally about 21.0 millimeters.

*Petal form.*—Round-shaped.

*Petal count.*—Nearly always 5.

*Petal texture.*—Smooth and glabrous.

*Petal color.*—Medium Pink (RHS Red Purple 65 B to C) when young, darkening with advancing senescence.

*Fragrance.*—Pronounced.

*Petal claw.*—Form. — The claw is considered to have a conic form with a slighty rounded extremity. Length. — Approximately 6.0 to 8.0 millimeters. Width. — Approximately 4.0 to 6.0 millimeters.

*Petal margins.*—Generally very slightly undulated.

*Petal apex.*—Generally. — The petal apices are generally dome-shaped.

*Flower pedicel.*—Length. — Considered medium and having an average length of approximately 4.0 millimeters. Diameter. — Considered average, approximately 2.0 millimeters. Color. — A medium brown (RHS Grey Brown N199 C to D).

*Floral nectaries.*—Color. — A green yellow (RHS Yellow 13 A to B or RHS Yellow Green 150 A to B).

*Calyx.*—Internal surface texture. — Smooth and glabrous. Color. — The outer surface of the calyx is considered of Purple-brown (RHS Greyed Purple 183 A) color.

*Sepals.*—Surface texture. — The outer surface has a short, fine pubescent texture. Size. — Average. Color. — Purple-brown (RHS Greyed Purple 183 A).

*Average number of stamens per flower.*—Approximately 39 stamens per flower.

*Anthers.*—Generally. — Small to medium in length. Color. — Red to orange-red color (approximately RHS Greyed Purple 178 A Group). Anthers are becoming yellow at maturity.

*Pollen production.*—Pollen is abundant, and has a yellow color (Approximately RHS Yellow Orange 17 B to C). The present variety is considered self fruitful (self-pollinating).

*Filaments.*—Size. — Variable in length, approximately 7.0 to 14.0 millimeters in length. Filaments length is generally equal to the pistil's length, if not slightly smaller.

*Color.*—Considered light pink (approximately RHS Red Purple 62 C to D) or pink (RHS Red Purple 73 A to B).

*Pistil.*—Number. — Usually 1. Generally. — Average in size. Length. — Approximately 17.0 to 20.0 millimeters including the ovary; Generally equal to filaments length, if not slightly superior to filaments in length. Color. — Considered a very pale green (RHS Yellow Green 150 D or RHS Yellow Green 151 D). Surface texture. — Glabrous.

Fruit:

*Maturity when described.*—Very firm ripe condition (shipping ripe).

*Date of first picking.*—Jun. 25, 2003.

*Date of last picking.*—Jul. 5, 2003. The date of harvest varies slightly with the prevailing climatic conditions. The 'NECTARFLORA' variety has an early date of picking, and a grouped maturity: only 2 harvests in 10 days were necessary. Last known picking times were from Jun. 18, 2006 to Jun. 26, 2006, then from Jun. 12 to Jun. 21, 2007, then from Jun. 18 to Jun. 26, 2008, then from Jun. 25 to Jun. 30, 2009.

*Size.*—Generally. — Considered large to very large for the period of maturity, and homogeneous in size.

*Average cheek diameter.*—Approximately 73.0 to 80.0 millimeters.

*Average axial diameter.*—Approximately 72.0 to 76.0 millimeters.

*Typical weight.*—Generally about 150.0 to 200.0 grams. This characteristic is high dependent upon the prevailing cultural practices, and therefore is not particularly distinctive of the variety.

*Fruit form.*—Generally. — Round. The fruit is generally uniform in symmetry, viewed from the suture's plane.

*Fruit suture.*—Wide-mouthed and slightly marked, extending from the base to the apex. No apparent callousing or stitching exists along the suture line.

*Suture.*—Color. — The suture has generally a color similar to the whole fruit color, a bright purple red (RHS Red Purple 59 A or RHS Red 46 A) on a pinky red background (RHS Red 38 C to B).

*Ventral surface.*—Form. — Smooth.

*Apex.*—Non-prominent, depressed, very small.

*Base.*—Slightly wide-mouthed, shallow.

*Stem cavity.*—Average depth of the stem cavity is about 1.0 cm. Average width is about 1.5 cm.

*Fruit skin.*—Thickness. — Considered very thick and strong, and tenacious to moderately tenacious to the flesh depending on stage of maturity. Texture. — Glabrous. Taste. — Semi-sweet, aromatic, with a high level of sugars. Tendency to crack. — None observed.

*Color.*—Blush color. — This blush color is an homogenous purple red (RHS Red Purple 59 A or RHS Red 46 A). The red blush covers 90% to 100% of the fruit skin surface. The percentage of the blush on the fruit skin surface can vary, and is generally dependant upon the prevailing conditions under which the fruit was grown. The blush color appears lately at the end of fruit development, reducing the risk that an anticipated harvest might be necessary. Ground color. — The ground color appears until 10% of the fruit skin surface, and is considered pink-washed red (RHS Red 38 C to B).

*Fruit stem.*—Medium in length, approximately 8.0 millimeters.

*Diameter.*—Approximately 4.0 millimeters.

*Color.*—Pale green (RHS Yellow Green 145A to 145 B).

*Flesh.*—Ripens. — Very evenly, homogenously, slowly. Texture. — Very firm, very dense, juicy at harvest maturity stage. Fibers. — Not fibrous. Aroma. — Pronounced. Eating quality. — Considered very good and aromatic. Flavor. — Considered semi-sweet. The Brix is generally superior to 12 and acidity comprised between 6 and 9 meq/100 ml. The flavor is considered very aromatic. Juice. — Very juicy at complete maturity. Brix. — Generally superior to 12.0 degrees but can reach higher degrees in other places. This characteristic varies slightly with the number of fruit per tree; prevailing cultural practices; and the surrounding climatic conditions. Flesh color. — White flesh (RHS White Group N155D) usually without any red pigmentation. Flesh can occasionally become pinky.

Stone:

*Type.*—Clingstone.

*Size.*—Considered medium for the variety. The stone size varies significantly depending upon the tree vigor, crop load and prevailing growing conditions.

*Length.*—Approximately 31.0 millimeters.

*Width.*—Approximately 23.0 millimeters.

*Diameter.*—Approximately 18.0 millimeters.

*Form.*—Elliptic.

*Base.*—Straight to slightly oblique.

*Apex.*—Shape. — The stone apex is short, with a small prominent tip. Stone Cavity: Considered medium size, with an elliptic-form and dimensions corresponding to the stone's dimensions.

*Stone surface.*—Surface texture. — The pit is transversely furrowed on its entire surface. Furrows are more pronounced toward the apex. The stone is pitted toward the base. Relief is prominent generally and present basally. Ridges. — The surface texture is generally characterized by more prominent ridges along the ventral edges and is more prominent at the apical tip.

*Ventral edge.*—Width. — Considered small to medium, and having a dimension of approximately 2.0 millimeters at mid-suture.

*Dorsal edge.*—Shape. — Grooved.

*Stone color.*—The color of the dry stone is generally considered an orange to red-brown (RHS Greyed Orange 173 C to D).

*Tendency to split.*—Splitting is absent or very low, depending on climatic conditions between blooming period and stone hardening.

*Kernel.*—Size. — The kernel is considered medium. Length. — Approximately 18.0 millimeters. Width. — Approximately 13.0 millimeters. Thickness. — Approximately 5.0 millimeters. Form. — Considered oblate and elliptic. Pellicle. — Slightly pubescent. Color. — The kernel skin is a light orange-yellow (RHS Greyed Orange 166 C) with darker streaks (RHS Greyed Orange 166 B). The almond, which is the seed of the kernel, is cream-white (RHS Orange White 159 D). The kernel and its embryo are mature at the time of fruit maturity.

Use: The subject variety 'NECTARFLORA' is considered to be a nectarine tree of the early season of maturity, and which produces fruits that are considered firm, attractively colored. Fruits have a semi-sweet taste and are excellent for uncooked consumption, crunchy or melting when at full maturity. Due to their flesh quality, firmness and density, they can also be commercialized as $4^{th}$ range product (packed fruit or fruit in bags for example). And they are also useful for both local and very long distance shipping.

Keeping quality: Remakable. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

Shipping quality: Considered very good. The fruit of the new nectarine variety showed minimal bruising of the flesh or skin damage after being subjected to normal harvesting and packing procedures. Its resistance to handling during harvest and packing and its long shelf life without alteration after harvest easily permit 3 weeks to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of nectarine tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

We claim:

1. A new and distinct variety of nectarine tree as illustrated and described, characterized by fruits of very long shelf life without alteration before and after harvesting, and with a semi-sweet white flesh of high eating quality and an attractive skin, with a very high percentage of red blush.

* * * * *